United States Patent [19]
Kumagai et al.

[11] Patent Number: 5,432,179
[45] Date of Patent: Jul. 11, 1995

[54] PIPERAZINE DERIVATIVES AND PHARMACEUTICALS CONTAINING THE SAME

[75] Inventors: Kazuhiro Kumagai; Masaaki Nagasawa; Hidenori Takahashi; Tooru Abe; Takeshi Omata; Yoshihide Segawa, all of Konan, Japan

[73] Assignee: Zeria Pharmaceutical Co., Ltd., Tokyo, Japan

[21] Appl. No.: 170,198

[22] PCT Filed: Jul. 2, 1992

[86] PCT No.: PCT/JP92/00833
§ 371 Date: Dec. 30, 1993
§ 102(e) Date: Dec. 30, 1993

[87] PCT Pub. No.: WO93/02062
PCT Pub. Date: Feb. 4, 1993

[30] Foreign Application Priority Data
Jul. 19, 1991 [JP] Japan .................. 3-203755

[51] Int. Cl.⁶ .................. A61K 31/495; A61K 31/55; C07D 295/155; C07D 243/08
[52] U.S. Cl. .................. 514/255; 514/218; 514/252; 544/364; 544/365; 544/366; 544/379; 544/397; 540/575
[58] Field of Search .................. 544/397; 514/255

[56] References Cited
U.S. PATENT DOCUMENTS
4,918,073  4/1990  Rüger et al. .................. 514/255

FOREIGN PATENT DOCUMENTS
3-246287  11/1991  Japan .
2056968   3/1981  United Kingdom .

OTHER PUBLICATIONS
Abstract for JP 3-246287 (Nov. 1, 1991).

Primary Examiner—Emily Bernard
Attorney, Agent, or Firm—Bacon & Thomas

[57] ABSTRACT

A piperazine derivative represented by the following formula:

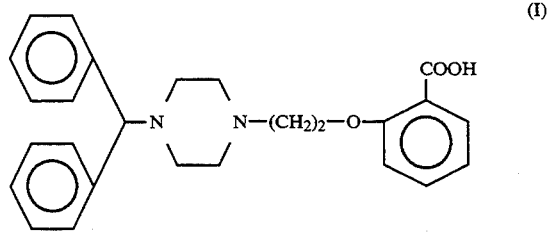

(I)

or a pharmaceutically acceptable salt thereof.

The compound according to the present invention has strong anti-histaminic and anti-allergic affects and a high degree of safety, and is useful as an anti-histaminic agent, an anti-allergic agent and/or an anti-asthmatic drug. Also disclosed are pharmaceutical compositions containing the compound of formula 1 and a method for the treatment of allergic diseases comprising administering the claimed compound.

4 Claims, No Drawings

PIPERAZINE DERIVATIVES AND PHARMACEUTICALS CONTAINING THE SAME

This application is a 371 of PCT/JP92/00833 filed Jul. 2,1992.

1. Technical Field

The present invention relates to novel piperazine derivatives and pharmaceuticals containing the same.

2. Background Art

Numerous piperazine derivatives have heretofore been synthesized and studied for various pharmacological effects. Among them, those having both antiallergic and antihistamic effects are known.

For example, compounds having the diphenylmethylpiperazine skeleton are disclosed in Japanese Patent Laid-Open Nos. 32474/1981, 149282/1982, 11072/1991 and the like. These compounds, however, are accompanied by one or more drawbacks such that their pharmacological effects are still insufficient and/or they are questionable in safety.

With a view toward preparing a compound having still better antiallergic and antihistamic effects and in addition, having a high degree of safety, the present inventors have carried out an extensive investigation. As a result, they have completed the present invention.

DISCLOSURE OF THE INVENTION

The present invention relates to a piperazine derivative represented by the following formula (I):

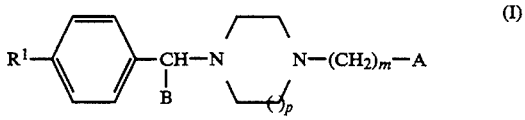

wherein B represents a phenyl or pyridinyl group, m stands for an integer of 2 or 3, p stands for an integer of 1 or 2, $R^1$ represents a hydrogen or halogen atom, A represents —COOR$^2$, —Y—(CH$_2$)$_n$, —R$^3$,

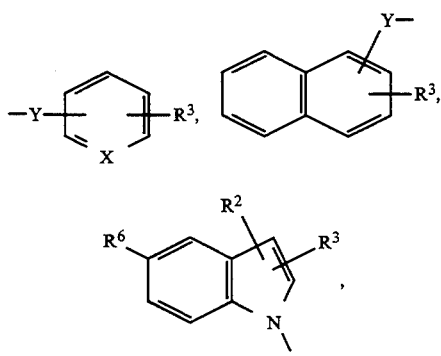

in which $R^2$ represents a hydrogen atom or a lower alkyl group, Y represents a sulfur or oxygen atom, NH or ←CONH— (← indicates a bond with a (CH$_2$)$_m$ group), n stands for an integer of 0 to 3, $R^3$ represents a cyano, amino, hydroxymethyl, 1H-tetrazole, 1-imidazolylcarbonyl, —CO—COOR$^4$, —(CH$_2$)$_l$—COOR$^4$ or —(CH$_2$)$_l$—CONH—R$^5$ group ($R^4$: hydrogen atom or lower alkyl group, l: integer of 0 to 3; and $R^5$: 1H-tetrazole, thiazol-2-yl, thiazolin-2-yl, triazol-5-yl, trimethoxyphenyl or 3,5-dimethyl-4-hydroxyphenyl group), X represents CH or a nitrogen atom and $R^6$ represents a hydrogen atom or a lower alkoxyl group,

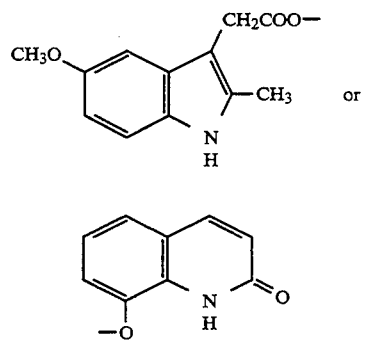

with the proviso that either case where $R^1$, B, p, m and A represent a hydrogen atom, a phenyl group, 1, 2 and —NH—C$_6$H$_4$—COOR$^4$, respectively, or where $R^1$, B, p, m and A represent a chlorine atom, a phenyl group, 1, 2 and —O—CH$_2$COOH, respectively is excluded; or a salt thereof.

In addition, the present invention also relates to an antihistamic agent and an antiallergic agent each containing the piperazine derivative (I) as an active ingredient.

In the formula (I), examples of the lower alkyl group represented by $R^2$ or $R^4$ include $C_{1-4}$ linear or branched alkyl groups, those of the lower alkoxyl group represented by $R^6$ include $C_{1-4}$ linear or branched alkyl groups, and those of the halogen atom represented by $R^1$ include chlorine, bromine, fluorine and iodine atoms.

The piperazine derivative (I) according to the present invention can be converted to a pharmaco-logically-acceptable salt thereof, for example, an acid-addition salt such as the hydrochloride, nitrate, sulfate, maleate, fumarate, oxalate, citrate, hydrobromate, succinate, sulfaminate, mandelate, malonate and phosphate or a base salt such as the sodium salt, potassium salt, lithium salt or calcium salt.

The compounds (I) according to the present invention may have stereoisomers such as optical isomers because they may contain an asymmetric carbon atom. It is to be noted that these isomers are all embraced by the present invention.

The compounds (I) according to the present invention have excellent antihistamic and antiallergic effects and also a high degree of safety as will be described later, so that they are effective as therapeutic agents for various allergic diseases, for example, as anti-inflammatory agents, therapeutics for nephritis, hepatitis or pancreatitis, preventives and/or therapeutics for respiratory diseases, and anti-asthmatic drugs.

BEST MODES FOR CARRYING OUT THE INVENTION

The compound (I) of this invention can be prepared, for example, in accordance with the following process:
Process A:

Process A:

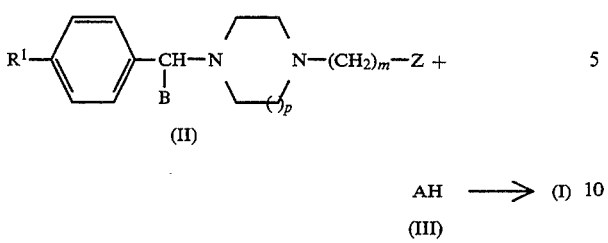

wherein $R^1$, B, p, m and A have the same meanings as defined above and Z is a halogen atom.

In other words, the compound (I) according to the present invention can be prepared by reacting a piperazine derivative represented by the formula (II) with a compound represented by the formula (III) in the presence of a base.

It is preferred to conduct the above reaction in a solvent which does not affect the reaction. Examples of the solvent include water; esters such as methyl acetate and ethyl acetate; ethers such as diethyl ether, diisopropyl ether, tetrahydrofuran and dioxane; ketones such as acetone and methyl ethyl ketone; halogenated hydrocarbons such as dichloromethane and chloroform; aromatic hydrocarbons such as benzene, toluene and xylene; acetonitrile; dimethylsulfoxide; and dimethylformamide. They may be used either singly or in combination. The reaction temperature may be varied depending on the starting compounds employed. In general, it is advantageous to select a temperature within a range of from 0° C. to a reflux temperature under normal pressure.

Examples of the base include carbonates such as potassium carbonate, sodium carbonate, sodium hydrogencarbonate and potassium hydrogencarbonate; alkali metal hydroxides such as potassium hydroxide, sodium hydroxide and lithium hydroxide; and organic bases such as triethylamine, diisopropylamine, DBU (1,8-diazabicyclo[5.4.0]-7-undecene).

When the compound represented by the formula (III) is a carboxylic acid ester, the corresponding carboxylic acid can be obtained by subjecting the invention compound (I), which has been prepared by the above reaction, to hydrolysis in a manner known per se in the art. The resulting carboxylic acid is then condensed with carbodiimidazole, 5-amino-1H-tetrazole, 2-aminothiazole, 2-aminothiazolidine, 5-aminotriazole, 3,4,5-trimethoxyaniline or 3,5-dimethyl-4-hydroxyaniline, leading to the preparation of another invention compound.

It is desirable to conduct the above condensation, in a manner known to date, in a solvent which does not affect the reaction. Examples of the solvent include esters such as methyl acetate and ethyl acetate; amides such as dimethylformamide and diethylformamide; ethers such as diethyl ether, diisopropyl ether, tetrahydrofuran and dioxane; halogenated hydrocarbons such as dichloromethane and chloroform; aromatic hydrocarbons such as benzene, toluene and xylene; acetonitrile; and dimethylsulfoxide. These solvents can be used either singly or in combination. The reaction temperature may be varied depending on the starting compounds employed. In general, it is advantageous to select a temperature within a range of from 0° C. to a reflux temperature under normal pressure.

When the compound represented by the formula (III) is a cyano-containing compound, the invention compound (I) prepared by the above reaction can be converted to another invention compound containing a 1H-tetrazole group by reacting the invention compound (I) with tri-n-butyltin azide in the presence of a base. It is desirable to conduct the reaction in a solvent which does not affect the reaction. Examples of the solvent include esters such as methyl acetate and ethyl acetate; ethers such as diethyl ether, diisopropyl ether, tetrahydrofuran and dioxane; halogenated hydrocarbons such as dichloromethane and chloroform; aromatic hydrocarbons such as benzene, toluene and xylene; and dimethylformamide. These solvents can be used either singly or in combination. The reaction temperature may be varied depending on the starting compounds employed. In general, it is advantageous to select a temperature within a range of from room temperature to a reflux temperature under normal pressure. As the base, those similar to the bases exemplified above can be employed.

Process B:

The invention compound can also be prepared by the following process:

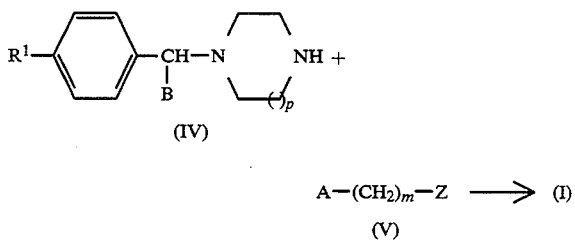

wherein Z, $R^1$, B, p, m and A have the same meanings as defined above.

In other words, the compound (I) according to the present invention can be prepared by subjecting a compound represented by the formula (IV) and a compound represented by the formula (V) to condensation in the presence of a base.

It is preferred to conduct the above reaction in a solvent which does not affect the reaction. Examples of the solvent include esters such as methyl acetate and ethyl acetate; ethers such as diethyl ether, diisopropyl ether, tetrahydrofuran and dioxane; ketones such as acetone and methyl ethyl ketone; halogenated hydrocarbons such as dichloromethane and chloroform; aromatic hydrocarbons such as benzene, toluene and xylene; acetonitrile; dimethylsulfoxide; and dimethylformamide. They can be used either singly or in combination. The reaction temperature may be varied depending on the starting compounds employed. In general, it is advantageous to select a temperature within a range of from 0° C. to a reflux temperature under normal pressure. As the base, bases similar to those exemplified in the Process A are usable.

When the compound represented by the formula (V) is a carboxylic acid ester or a cyano-containing compound, the invention compound so obtained can be converted to a corresponding invention compound of another type by treating it in a similar manner to Process A.

When the starting compound (II) or (IV) has an asymmetric carbon atom in Process A or Process B, the invention compound (I) so obtained includes corresponding stereoisomers.

Among the invention compounds (I) obtained as de-scribed above, the followings are representatives ones except for the compounds to be described in Examples.

2-[3-[4-[(4-Chlorophenyl)phenylmethyl]-1-piperazinyl]-propoxy]-N-3,4,5-trimethoxyphenylbenzamide 2-[3-[4-[(4-Chlorophenyl)phenylmethyl]-1-piperazinyl]-propoxy]-N-(3,5-dimethyl-4-hydroxyphenyl)-benzamide 3-[3-[4-[(4-Chlorophenyl)phenylmethyl]-1-piperazinyl]-propoxy]benzoic acid 3-[3-[4-[(4-Chlorophenyl)phenylmethyl]-1-piperazinyl]-propoxy]-N-1H-tetrazol-5-yl-benzamide 2-[[3-[4-[(4-Chlorophenyl)phenylmethyl]-1-piperazinyl]propyl]thio]benzoic acid 2-[[3-[4-[(4-Chlorophenyl)phenylmethyl]-1-piperazinyl]propyl]thio]-N-1H-tetrazol-5-yl-benzamide 2-[3-[4-[(4-Chlorophenyl)phenylmethyl]-1-piperazinyl]-propoxy]nicotinic acid 2-[3-[4-[(4-Chlorophenyl)phenylmethyl]-1-piperazinyl]-propoxy]-N-1H-tetrazol-5-yl-nicotinamide 3-[2-[4-[(4-Chlorophenyl)phenylmethyl]-1-homopiperazinyl]ethoxy]benzoic acid 3-[2-[4-[(4-Chlorophenyl)phenylmethyl]-1-homopiperazinyl]ethyl]-N-1H-tetrazol-5-yl-benzamide Ethyl 4-[[2-[4-[(4-chlorophenyl)phenylmethyl]-1-homopiperazinyl]ethyl]thio]benzoate 4-[[2-[4-[(4-Chlorophenyl)phenylmethyl]-1-homopiperazinyl]ethyl]thio]-N-1H-tetrazol-5-yl-benzamide 3-[2-[4-[(4-Chlorophenyl)phenylmethyl]-1-homopiperazinyl]ethoxy]phenylacetic acid 3-[2-[4-[(4-Chlorophenyl)phenylmethyl]-1-homopiperazinyl]ethoxy]-N-1H-tetrazol-5-yl-phenylacetamide 4-[2-[4-[(4-Chlorophenyl)phenylmethyl]-1-homopiperazinyl]ethoxy]-N-1H-tetrazol-5-yl-anthranylamide Propyl 2-[2-[4-[(4-chlorophenyl)phenylmethyl]-1-homopiperazinyl]ethoxy]nicotinate 2-[2-[4-[(4-Chlorophenyl)phenylmethyl]-1-homopiperazinyl]ethoxy]-N-1H-tetrazol-5-yl-nicotinamide 2-[[2-[4-[(4-Chlorophenyl)phenylmethyl]-1-homopiperazinyl]ethyl]thio]acetic acid 1-[2-[4-[(4-Chlorophenyl)phenylmethyl]-1-homopiperazinyl]ethyl]-3-indolecarboxylic acid 1-[2-[4-[(4-Chlorophenyl)phenylmethyl]-1-homopiperazinyl]ethyl]-N-1H-tetrazol-5-yl-3-indoleamide Butyl 4-[3-[4-[(4-chlorophenyl)phenylmethyl]-1-homopiperazinyl]propoxy]benzoate 4-[3-[4-[(4-Chlorophenyl)phenylmethyl]-1homopiperazinyl]propoxy]-N-1H-tetrazol-5-yl-benzamide Methyl 2-[3-[4-[(4-chlorophenyl)phenylmethyl]-1-homopiperazinyl]propoxy]naphthoate 2-[3-[4-[(4-Chlorophenyl)phenylmethyl]-1-homopiperazinyl]propoxy]naphthoic acid 4-[3-[4-[(4-Chlorophenyl)phenylmethyl]-1-homopiperazinyl]propoxy]-N-1H-tetrazol-5-yl-naphthamide 2-[2-[4-(Diphenylmethyl)-1-piperazinyl]ethoxy]-N-1H-triazol-5-yl-benzamide 2-[2-[4-(Diphenylmethyl)-1-piperazinyl]ethyl]thio]-N-1H-tetrazol-5-yl-benzamide 2-[2-[4-(Diphenylmethyl)-1-piperazinyl]ethoxy]-N-1H-tetrazol-5-yl-nicotinamide 1-[2-[4-(Diphenylmethyl)-1-piperazinyl]ethyl]-N-1H-tetrazol-5-yl-2-indoleamide 4-[2-[4-(Diphenylmethyl)-1-piperazinyl]ethoxy]-[N-1H-tetrazol-5-yl]-benzene 4-[2-[4-(Diphenylmethyl)-1-piperazinyl]ethoxy]-benzamide 4-[3-[4-(Diphenylmethyl)-1-piperazinyl]propoxy]-N-3,4,5-trimethoxyphenyl-benzamide 4-[3-[4-(Diphenylmethyl)-1-piperazinyl]propoxy]-thiazol-2-yl-benzamide 4-[3-[4-(Diphenylmethyl)-1-piperazinyl]propyl]-thio]-benzoic acid 4-[3-[4-(Diphenylmethyl)-1-piperazinyl]propyl]-thio]-N-1H-tetrazol-5-yl-benzamide 2-[3-[4-(Diphenylmethyl)-1-piperazinyl]propoxy]-anthranilic acid 2-[3-[4-(Diphenylmethyl)-1-piperazinyl]propoxy]-N-1H-tetrazol-5-yl-anthranilamide 2-[3-[4-(Diphenylmethyl)-1-piperazinyl]propoxy]-nicotinic acid 2-[3-[4-(Diphenylmethyl)-1-piperazinyl]propoxy]-N-1H-tetrazol-5-yl-nicotinamide 1-[3-[4-(Diphenylmethyl)-1-piperazinyl]propyl]-2-indolecarboxylic acid 1-[3-[4-(Diphenylmethyl)-1-piperazinyl]propyl]-2-N-1H-tetrazol-5-yl-indoleamide 4-[3-[4-(Diphenylmethyl)-1-piperazinyl]propoxy]-benzonitrile Butyl 2-[[3-[4-(diphenylmethyl)-1-piperazinyl]-propyl]thio]acetate -2-[[3-[4-(Diphenylmethyl)-1-piperazinyl]propyl]-thio]acetic acid 2-[3-[4-(Diphenylmethyl)-1-piperazinyl]propoxy]-N-1H-tetrazol-5-yl-acetamide 1-[3-[4-(Diphenylmethyl)-1-piperazinyl]propoxy]-naphthoic acid 1-[3-[4-(Diphenylmethyl)-1-piperazinyl]propoxy]-N-1H-tetrazol-5-yl-naphthoamide Ethyl 2-[3-[4-(diphenylmethyl)-1-homopiperazinyl]-propoxy]benzoate 2-[3-[4-(Diphenylmethyl)-1-homopiperazinyl]-propoxy]-N-1H-tetrazol-5-yl-benzamide Methyl 2-[3-[4-(diphenylmethyl)-1-homopiperazinyl]-propoxy]naphthoate 2-[3-[4-(Diphenylmethyl)-1-homopiperazinyl]-propoxy]naphthoic acid 2-[3-[4-(Diphenylmethyl)-1-homopiperazinyl]-propoxy]-N-1H-tetrazol-5-yl-naphthoamide Propyl 3-[2-[4-[2-(4-chlorophenyl)pyridylmethyl]-1-piperazinyl]ethoxy]benzoate 3-[2-[4-[2-(4-Chlorophenyl)pyridylmethyl]-1-piperazinyl]ethoxy]-N-1H-tetrazol-5-yl-benzamide 2-[[2-[4-[2-(4-Chlorophenyl)pyridylmethyl]-1-piperazinyl]ethyl]thio]benzoic acid 2-[[2-[4-[2-(4-Chlorophenyl)pyridylmethyl]-1-piperazinyl]ethyl]thio]-N-1H-tetrazol-5-yl-benzamide 2-[2-[4-[2-(4-Chlorophenyl)pyridylmethyl]-1-piperazinyl]ethoxy]anthranilic acid 2-[2-[4-[2-(4-Chlorophenyl)pyridylmethyl]-1-piperazinyl]ethoxy]-N-1H-tetrazol-5-yl-anthranilamide 1-[2-[4-[2-(4-Chlorophenyl)pyridylmethyl]-1piperazinyl]ethyl]-3-ethoxycarbonyl-indole
1-[2-[4-[2-(4-Chlorophenyl)pyridylmethyl]-1-piperazinyl]ethyl]-N-1H-tetrazol-5-yl-3-indoleamide
3-[2-[4-[2-(4-Chlorophenyl)pyridylmethyl]-1-piperazinyl]ethoxy]benzonitrile
4-[2-[4-[2-(4-Chlorophenyl)pyridylmethyl]-1-piperazinyl]ethoxy]benzoylimidazole
2-[2-[4-[2-(4-Chlorophenyl)pyridylmethyl]-1-piperazinyl]ethoxy]-N-1H-tetrazol-5-yl-acetamide
2-[2-[4-[2-(4-Chlorophenyl)pyridylmethyl]-1-piperazinyl]ethoxy]-1H-tetrazole-5-ylmethyl
4-[3-[4-[2-(4-Chlorophenyl)pyridylmethyl]-1-piperazinyl]propoxy]benzoic acid
4-[3-[4-[2-(4-Chlorophenyl)pyridylmethyl]-1-piperazinyl]propyl]-N-1H-tetrazol-5-yl-benzamide
Butyl 3-[2-[4-[2-(4-chlorophenyl)pyridylmethyl]-1-homopiperazinyl]ethoxy]benzoate
3-[2-[4-[2-(4-Chlorophenyl)pyridylmethyl]-1-homopiperazinyl]ethoxy]-N-1H-tetrazol-5-yl-benzamide
Ethyl 1-[2-[4-[2-(4-chlorophenyl)pyridylmethyl]-1-homopiperazinyl]ethoxy]naphthoate
1-[2-[4-[2-(4-Chlorophenyl)pyridylmethyl]-1-homopiperazinyl]ethoxy]naphthoic acid
1-[2-[4-[2-(4-Chlorophenyl)pyridylmethyl]-1homopiperazinyl]ethoxy]-N-1H-tetrazol-5-yl-naphthoamide
2-[3-[4-[2-(4-Chlorophenyl)pyridylmethyl]-1-homopiperazinyl]propoxy]benzoic acid
2-[3-[4-[2-(4-Chlorophenyl)pyridylmethyl]-1-homopiperazinyl]propoxy]-N-1H-tetrazol-5-yl-benzamide
2-[3-[4-[2-(4-Chlorophenyl)pyridylmethyl]-1-homopiperazinyl]propoxy]naphthoic acid
2-[3-[4-[2-(4-Chlorophenyl)pyridylmethyl]-1-homopiperazinyl]propoxy]-N-1H-tetrazol-5-yl-naphthoamide
2-[[2-[4-(2-Phenyl-pyridylmethyl)-1-piperazinyl]-ethyl]-thio]benzoic acid
2-[[2-[4-(2-Phenyl-pyridylmethyl)-1-piperazinyl]-ethyl]-thio]-N-1H-tetrazol-5-yl-benzamide
2-[2-[4-(2-Phenyl-pyridylmethyl)-1-piperazinyl]-ethoxy]anthranilic acid
2-[2-[4-(2-Phenyl-pyridylmethyl)-1-piperazinyl]-ethoxy]-N-1H-tetrazol-5-yl-anthranilamide
2-[2-[4-(2-Phenyl-pyridylmethyl)-1-piperazinyl]-ethoxy]nicotinic acid
2-[2-[4-(2-Phenyl-pyridylmethyl)-1-piperazinyl]-ethyl]-N-1H-tetrazol-5-yl-nicotinamide
Methyl 2-[3-[4-(2-phenyl-pyridylmethyl)-1-piperazinyl]propoxy]benzoate
2-[3-[4-(2-phenyl-pyridylmethyl)-1-piperazinyl]-propoxy]-N-1H-tetrazol-5-yl-benzamide
Propyl 2-[3-[4-(2-phenyl-pyridylmethyl)-1-piperazinyl]-propoxy]naphthoate
2-[3-[4-(2-Phenyl-pyridylmethyl)-1-piperazinyl]-propoxy]naphthoic acid
2-[3-[4-(2-Phenyl-pyridylmethyl)-1-piperazinyl]-propoxy]-N-1H-tetrazol-5-yl-naphthoamide
3-[2-[4-(2-Phenyl-pyridylmethyl)-1-homopiperazinyl]ethoxy]benzoic acid
3-[2-[4-(2-Phenyl-pyridylmethyl)-1-homopiperazinyl]ethoxy]-N-1H-tetrazol-5-yl-benzamide
Methyl 1-[2-[4-(2-phenyl-pyridylmethyl)-1-homopiperazinyl]ethoxy]naphthoate
1-[2-[4-(2-Phenyl-pyridylmethyl)-1-homopiperazinyl]ethoxy]naphthoic acid
1-[2-[4-(2-Phenyl-pyridylmethyl)-1-homopiperazinyl]ethoxy]-N-1H-tetrazol-5-yl-naphthoamide
Ethyl 2-[3-[4-(2-phenyl-pyridylmethyl)-1-homopiperazinyl]propoxy]benzoate
2-[3-[4-(2-Phenyl-pyridylmethyl)-1-homopiperazinyl]propoxy]-N-1H-tetrazol-5-yl-benzamide
Ethyl 2-[3-[4-(2-phenyl-pyridylmethyl)-1-homopiperazinyl]propoxy]naphthoate
2-[3-[4-(2-Phenyl-pyridylmethyl)-1-homopiperazinyl]propoxy]naphthoic acid
2-[3-[4-(2-Phenyl-pyridylmethyl)-1-homopiperazinyl]propoxy]-N-1H-tetrazol-5-yl-naphthoamide The compound (I) according to the present invention can be formulated into dosage forms suited for oral administration or parenteral administration by adding one or more pharmaceutically-acceptable auxiliary agents thereto.

Solid dosage forms for oral administration include tablets, powders, granules and capsules. The invention compound (I) can be formulated into such a solid preparation by combining it with one or more suitable additives such as excipients, e.g., lactose, mannitol, corn starch or crystalline cellulose; binders, e.g., a cellulose derivative, gum arabic or gelatin; disintegrators, e.g., calcium carboxymethylcellulose; and lubricants such as talc and magnesium stearate. The solid preparation so obtained can be converted into an enteric coated one by coating it with a coating base material such as hydroxypropylmethylcellulose phthalate, hydroxypropylmethylcellulose acetate succinate, cellulose acetate phthalate or a methacrylate copolymer.

Exemplary liquid preparations for oral administration include emulsions, solutions, suspensions, syrups and elixirs. The compound (I) according to the present invention can be prepared in the form of a liquid preparation by combining an inert diluent such as purified water or ethanol. In addition to the inert diluent, auxiliary agents such as a humectant and a suspending agent, a sweetener, a taste improver, an aromatic agent and/or an antiseptic can be added. The compound can also be used in the form of an aerosol preparation which is formulated in a manner known per se in the art.

Examples of the liquid preparation for parenteral administration include injections. The invention compound (I) can be formulated into the form of an injection by combining the compound with water, ethanol, glycerin and a conventional surfactant. Further, the compound can also be used in the form of a surface application drug such as an inhalation, liquid for external use, ophthalmic solution, nasal drops or ointment.

The dosage of the compound (I) of the present invention varies depending on the age, weight, conditions, therapeutic effects, administration method, administration period, etc. In general, it is desirable to orally administer the compound (I) at a daily dosage of 1–500 mg/day, particularly 5–50 mg/day, in 1–3 portions a day or to parenterally administer it at a dosage of 0.1–500 mg/day in one to several portions a day.

EXAMPLE

The present invention will hereinafter be described more specifically by the following examples. It is, however, to be borne in mind that the present invention is by no means limited to or by them. In each table, Ph and Py indicate a phenyl group and a 2-pyridinyl group, respectively.

EXAMPLE 1

Methyl 3-[2-[4-[(4-chlorophenyl)phenylmethyl]-1-piperazinyl]ethoxy]benzoate

In acetone, 16.0 g (38 mmol) of 2-[4-[(4-chlorophenyl)phenylmethyl]-1-piperazinyl]ethyl chloride.-dihydrochloride and 18.3 g of potassium carbonate were suspended, followed by the addition of 6.9 g (45 mmol) of methyl 3-hydroxybenzoate. The resulting suspension was refluxed at 70° C. for 24 hours. After the reaction mixture was allowed to cool down, 200 ml of water were added, followed by extraction with 200 ml portions of ethyl acetate twice. The ethyl acetate layers were washed with water and dried over anhydrous magnesium sulfate. The solvent was thereafter distilled off. The residue so obtained was purified by chromatography on a silica gel column (ethyl acetate:n-hexane=1:1), whereby 12 g of the title compound were obtained.

Yield: 68%. Melting point (decomposition point): 200°–205° C. (dihydrochloride) MS (m/z): 464(M+) IR (nujol) cm−1: 3400, 2350, 1710 NMR (DMSO-d6) δ: (oxalate) 2.55(4H,brs), 3.23(4H,brs), 3.40(2H,t), 3.85(3H,s), 4.35(2H,t), 4.47 (1H,s), 7.22–7.59(13H,m)

EXAMPLE 2

3-[2-[4-[(4-Chlorophenyl)phenylmethyl]-1-piperazinyl]ethoxy]benzoic acid

In 200 ml of ethanol, 10 g of the methyl 3-[2-[4-[(4-chlorophenyl)phenylmethyl]-1-piperazinyl]-ethoxy]-benzoate obtained in Example 1 and 50 ml of 10% sodium hydroxide were dissolved, followed by stirring at 50° C. for one hour. After the reaction mixture was allowed to cool down, the solvent was distilled off under reduced pressure. Water (200 ml) was added to the residue, followed by the addition of acetic acid to adjust its pH to 4.0. The resulting mixture was extracted with 200 ml portions of ethyl acetate twice. The ethyl acetate layers so obtained were washed with water and then dried over anhydrous magnesium sulfate. The solvent was distilled off under reduced pressure. The residue so obtained was purified by chromatography on a silica gel column (chloroform:methanol=10:1), whereby 6.6 g of the title compound were obtained.

Yield: 69%. Melting point (decomposition point): 202°–203° C. MS (m/z): 450(M+) IR (nujol) cm−: 3400, 1705, 1580 NMR (DMSO-d6 ) δ: 2.77(1H,brs), 3.35–3.42(8H,m), 3.50(2H,t), 4.46(2H,t), 4.51(1H,s), 7.22–7.58(13H,m)

EXAMPLES 3–39

The compounds of Examples 3–39 shown in Tables 1–8 were each obtained in accordance with the procedures of Example 1 or Example 2. The names of the respective compounds will be described below.

EXAMPLE 3

Methyl 2-[2-[4-[(4-chlorophenyl)phenylmethyl]-1-piperazinyl]ethoxy]benzoate

EXAMPLES 4 & 5

2-[2-[4-[(4-Chlorophenyl)phenylmethyl]-1-piperazinyl]ethoxy]benzoic acid

EXAMPLE 6

Methyl 4-[2-[4-[(4-chlorophenyl)phenylmethyl]-1-piperazinyl]ethoxy]benzoate

EXAMPLE 7

4-[2-[4-[(4-Chlorophenyl)phenylmethyl]-1-piperazinyl]ethoxy]benzoic acid

EXAMPLE 8

Methyl 2-[2-[4-(diphenylmethyl)-1-piperazinyl]-ethoxy]benzoate

EXAMPLE 9

2-[2-[4-(Diphenylmethyl)-1-piperazinyl]ethoxy]-benzoic acid

EXAMPLE 10

Methyl 2-[3-[4-[(4-chlorophenyl)phenylmethyl]-1-piperazinyl]propoxy]benzoate

EXAMPLE 11

2-[3-[4-[(4-Chlorophenyl)phenylmethyl]-1-piperazinyl]propoxy]benzoic acid

EXAMPLE 12

2-[2-[4-[(4-Chlorophenyl)phenylmethyl]-1-piperazinyl]ethoxy]benzyl alcohol

EXAMPLE 13
2-[2-[4-[(4-Chlorophenyl)phenylmethyl]-1-piperazinyl]ethoxy]benzonitrile

EXAMPLE 14
3-[2-[4-[(4-Chlorophenyl)phenylmethyl]-1-piperazinyl]ethoxy]benzonitrile

EXAMPLE 15
[3-[4-(Diphenylmethyl)-1-piperazinyl]N-propionyl]anthranilic acid

EXAMPLE 16
Methyl 1-[2-[4-[(4-chlorophenyl)phenylmethyl]-1-piperazinyl]ethoxy]naphthoate

EXAMPLE 17
1-[2-[4-[(4-Chlorophenyl)phenylmethyl]-1-piperazinyl]ethoxy]naphthoic acid

EXAMPLE 18
Methyl 2-[2-[4-[(4-chlorophenyl)phenylmethyl]-1-piperazinyl]ethoxy]naphthoate

EXAMPLE 19
2-[2-[4-[(4-Chlorophenyl)phenylmethyl]-1-piperazinyl]ethoxy]naphthoic acid

EXAMPLE 20
3-[1-[2-[4-[(4-Chlorophenyl)phenylmethyl]-1-piperazinyl]ethoxycarbonylmethyl]-2-methyl-5-methoxy-indole

EXAMPLE 21
1-[2-[4-[(4-Chlorophenyl)phenylmethyl]-1-piperazinyl]ethyl]-2-methyloxycarbonyl-indole

EXAMPLE 22
1-[2-[4-[(4-Chlorophenyl)phenylmethyl]-1-piperazinyl]ethyl]-3-indolecarboxylic acid

EXAMPLE 23
Methyl 1-[2-[4-[(4-chlorophenyl)phenylmethyl]-1-piperazinyl]ethyl]-2-methyl-5-methoxy-3-indole-acetate

EXAMPLE 24
1-[2-[4-[(4-Chlorophenyl)phenylmethyl]-1-piperazinyl]ethyl]-2-methyl-5-methoxy-3-indoleacetic acid

EXAMPLE 25
1-[2-[4-[(4-Chlorophenyl)phenylmethyl]-1-piperazinyl]ethyl]-2-indolecarboxylic acid

EXAMPLE 26
2-[2-[4-[(4-Chlorophenyl)phenylmethyl]-1-piperazinyl]ethoxy]phenylacetic acid

EXAMPLE 27
Methyl 2-[2-[4-[(4-chlorophenyl)phenylmethyl]-1-piperazinyl]ethoxy]phenylacetate

EXAMPLE 28
Methyl 2-[2-[4-[(4-chlorophenyl)phenylmethyl]-1-piperazinyl]ethoxy]nicotinate

EXAMPLE 29
2-[2-[4-[(4-Chlorophenyl)phenylmethyl]-1-piperazinyl]ethoxy]nicotinic acid

EXAMPLE 30
8-[2-[4-(Diphenylmethyl)-1-piperazinyl]ethoxy]-quinolin-N-(1H)-2-one

EXAMPLE 31
2-[2-[4-[2-(4-Chlorophenyl)pyridylmethyl]-1-piperazinyl]ethoxy]benzoic acid

EXAMPLE 32
Methyl 2-[2-[4-[(4-chlorophenyl)phenylmethyl]-1-homopiperazinyl]ethoxy]benzoate

EXAMPLE 33
2-[2-[4-[(4-Chlorophenyl)phenylmethyl]-1-homopiperazinyl]ethoxy]benzoic acid

EXAMPLE 34
Methyl 2-[2-[4-(2-phenyl-pyridylmethyl)-1-piperazinyl]ethoxy]benzoate

EXAMPLE 35
2-[2-[4-(2-Phenyl-pyridylmethyl)-1-piperazinyl]ethoxy]benzoic acid

EXAMPLE 36
Ethyl 4-[4-[(4-chlorophenyl)phenylmethyl]-1-piperazinyl]butyrate

EXAMPLE 37
4-[4-[(4-chlorophenyl)phenylmethyl]-1-piperazinyl]butyric acid

EXAMPLE 38
Methyl 2-[2-[4-(diphenyl)-1-homopiperazinyl]ethoxy]benzoate

EXAMPLE 39
2-[2-[4-(Diphenyl)-1-homopiperazinyl]ethoxy]benzoic acid

TABLE 1

| EX. | R¹ | B | m | p | A | Melting point(°C.) | MS(M⁺) | IR(cm⁻¹), NMR(ppm) |
|---|---|---|---|---|---|---|---|---|
| 3 | Cl | Ph | 2 | 1 | 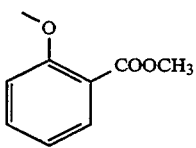 | Decomposition point 210-214 (Dihydrochloride) | 464 | IR(nujol):1720 NMR(CDCl$_3$):(2HCl)3.56(4H, brs), 3.83(3H, s), 4.04(2H, t), 4.40(4H, brs), 4.63(2H, t), 5.00(1H, s), 6.95–7.88(13H, m) |

TABLE 1-continued

| EX. | R¹ | B | m | p | A | Melting point(°C.) | MS(M+) | IR(cm⁻¹), NMR(ppm) |
|---|---|---|---|---|---|---|---|---|
| 4 | Cl | Ph | 2 | 1 | 2-methoxybenzoic acid group (COOH ortho to OMe) | Decomposition point 216–218 (Dihydrochloride) | 450 | IR(nujol):1690 NMR(CDCl₃):2.34(4H, brs), 2.70(2H, t), 2.97(4H, brs), 3.94(1H, s), 4.03(2H, brs), 6.78–7.81(13H, m) |
| 5 | Cl | Ph | 2 | 1 | 2-methoxybenzoic acid group | 193–195 (½ Fumarate) | 450 | IR(nujol):1690 NMR(DMSO-d₆):2.36(4H, brs), 2.70(4H, brs), 2.82(2H, t), 4.25(2H, t), 4.33(1H, s), 6.62(1H, s), 6.98–7.61(13H, m), 8.25(2H, brs) |
| 6 | Cl | Ph | 2 | 1 | 4-methoxy, COOCH₃ para | Decomposition point 197–199 (Dihydrochloride) | 464 | IR(nujol):3400, 1720 NMR(DMSO-d₆):(oxalate) 2.54(4H, brs), 3.22(4H, brs), 3.40(2H, t), 4.37(2H, t), 4.47(1H, s), 7.05–7.93(13H, m) |
| 7 | Cl | Ph | 2 | 1 | 4-methoxy, COOH para | Decomposition point 230–232 (Dihydrochloride) | 450 | IR(nujol):3400, 1700 NMR(DMSO-d₆):2.77(1H, brs), 3.34(8H, brs), 3.50(2H, brs), 4.51(3H, brs), 7.05–7.92(13H, m) |

TABLE 2

| EX. | R¹ | B | m | p | A | Melting point(°C.) | MS(M+) | IR(cm⁻¹), NMR(ppm) |
|---|---|---|---|---|---|---|---|---|
| 8 | H | Ph | 2 | 1 | 2-methoxy, COOCH₃ | Decomposition point 211–213 (Dihydrochloride) | 430 | IR(nujol):3380, 1720 NMR(CDCl₃):(2HCl)3.58(4H, brs), 3.83(3H, s), 4.01(4H, brs), 4.48(2H, t), 4.61(2H, t), 5.02(1H, s), 6.95–7.91(14H, m) |
| 9 | H | Ph | 2 | 1 | 2-methoxy, COOH | 178–179 (Maleate) | 416 | IR(nujol):1675 NMR(DMSO-d₆):2.51(4H, brs), 3.38(4H, brs), 3.46(2H, t), 4.37(2H, t), 4.46(1H, s), 7.04–7.70(14H, m) |
| 10 | Cl | Ph | 3 | 1 | 2-methoxy, COOCH₃ | 114–117 (Maleate) | 478 | NMR(DMSO-d₆):2.15(2H, m), 2.30(2H, m), 2.83(2H, brs), 3.15(2H, brs), 3.31(2H, t), 3.50(2H, m), 3.78(3H, s), 4.13(2H, t), 4.56(1H, s), 6.14(4H, s), 7.05–7.73(13H, m) |
| 11 | Cl | Ph | 3 | 1 | 2-methoxy, COOH | — powder | 464 | IR(nujol):3420, 1680 NMR(DMSO-d₆):(2HCl)2.21(2H, t), 3.15(4H, brs), 3.35(4H, brs), 3.57(1H, s), 3.60(2H, m), 4.14(2H, t), 7.03–7.72(14H, m) |

TABLE 2-continued

| EX. | R¹ | B | m | p | A | Melting point(°C.) | MS(M⁺) | IR(cm⁻¹), NMR(ppm) |
|---|---|---|---|---|---|---|---|---|
| 12 | Cl | Ph | 2 | 1 | 2-methoxybenzyl alcohol (2-OCH₃, CH₂OH-phenyl) | powder | 436 | IR(nujol):3350 NMR(CDCl₃):2.42(4H, brs), 2.54 (4H, brs), 2.63(1H, s), 2.73(2H, brs), 4.20(2H, brs), 4.22(1H, s) 4.60(2H, s), 6.88–7.35(13H, m) |

TABLE 3

| EX. | R¹ | B | m | p | A | Melting point(°C.) | MS(M⁺) | IR(cm⁻¹), NMR(ppm) |
|---|---|---|---|---|---|---|---|---|
| 13 | Cl | Ph | 2 | 1 | 2-methoxy, 3-CN phenyl (—O—C₆H₄(CN)) | Decomposition point 160 (Oxalate) | 431 | IR(nujol):2220 NMR(DMSO-d₆):(Oxalate)2.52 (4H, m), 3.25(4H, m), 3.41(2H, t), 4.46(2H, t), 4.49(1H, s), 7.13–7.75(13H, m) |
| 14 | Cl | Ph | 2 | 1 | 3-cyanophenoxy (—O—C₆H₄—CN) | 168–170 | 431 | IR(nujol):2220, 1680 NMR(DMSO-d₆):(fumarate)2.51 (4H, brs), 3.30(4H, brs), 3.54 (2H, t), 4.39(2H, t), 4.55(1H, s), 6.15(4H, s), 7.24–7.53(13H, m) |
| 15 | H | Ph | 2 | 1 | —CONH—C₆H₄—COOH | Decomposition point 223 | 443 | IR(nujol):3580, 3450, 1670 NMR(DMSO-d₆):2.70–3.10(6H, m), 2.40–2.50(12H, m), 3.14(2H, t) 4.36(1H, s), 7.01–7.43(12H, m), 7.95–7.98(1H, m), 8.45–8.48(1H, m) |
| 16 | Cl | Ph | 2 | 1 | 2-(naphthalenyloxy)-1-COOCH₃ | Decomposition point 177–180 (Dihydrochloride) | 514 | IR(nujol):3400, 1720, 1600 NMR(CDCl₃):3.54(4H, brs), 3.83 (4H, brs), 4.03(3H, s), 4.43 (2H, brs), 4.72(2H, brs), 4.95 (1H, s), 7.28–7.93(15H, m) |
| 17 | Cl | Ph | 2 | 1 | 2-(naphthalenyloxy)-1-COOH | 130–131 | 500 | IR(nujol):3200, 1580, 1410 NMR(CDCl₃):2.42(4H, brs), 2.53(4H, brs), 2.68(2H, t), 4.22(1H, s), 4.51(2H, t), 7.10–8.35(15H, m) |

TABLE 4

| EX. | R¹ | B | m | p | A | Melting point(°C.) | MS(M⁺) | IR(cm⁻¹), NMR(ppm) |
|---|---|---|---|---|---|---|---|---|
| 18 | Cl | Ph | 2 | 1 | 1-(naphthalenyloxy)-2-COOCH₃ | Decomposition point 197–200 (Dihydrochloride) | 514 | IR(nujol):3500, 1710, 1600 NMR(CDCl₃):3.75(2H, t), 3.96 (3H, s), 4.12(4H, brd), 4.53 (4H, brd), 4.63(2H, t), 5.05 (1H, s), 7.36–8.33(15H, m) |
| 19 | Cl | Ph | 2 | 1 | 1-(naphthalenyloxy)-2-COOH | 192–194 (Dihydrochloride) | 500 | IR(nujol):3450, 1690, 1600 NMR(DMSO-d₆):(2HCl)3.03 (2H, brs), 3.76(5H, brs), 4.45(6H, brt), 7.40–8.34(16H, m) |
| 20 | Cl | Ph | 2 | 1 | 5-methoxy-2-methyl-3-(CH₂COO—)-indole | — (amorphous) | 531 | NMR(DMSO-d₆):2.18(4H, brs), 2.29 (3H, s), 2.35(4H, brs), 2.51 (2H, t), 3.59(2H, s), 3.70(3H, s), 4.07(2H, t), 4.21(1H, s), 6.57–7.42(12H, m), 10.65(1H, brs) |

TABLE 4-continued

| EX. | R¹ | B | m | p | A | Melting point(°C.) | MS(M⁺) | IR(cm⁻¹), NMR(ppm) |
|---|---|---|---|---|---|---|---|---|
| 21 | Cl | Ph | 2 | 1 | 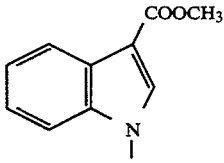 (indole-3-COOCH₃) | — (foam) | 487 | NMR(DMSO-d₆):2.25(4H, brs), 2.46(4H, brs), 2.67(2H, t), 3.81 (3H, s), 4.24(1H, s), 4.30(2H, t), 7.15–7.57(11H, m), 7.54–7.57(1H, m), 8.03–8.06(1H, m), 8.12(1H, s) |
| 22 | Cl | Ph | 2 | 1 | 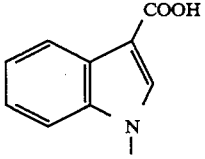 (indole-3-COOH) | Decomposition point 105–110 | 474 | IR(nujol):3350, 1680 NMR(DMSO-d₆):2.28(4H, brs), 2.70(2H, t), 3.35(4H, brs), 4.28(1H, s), 4.32(2H, t), 7.16–7.99(14H, m), 8.03(1H, s) |

TABLE 5

| Ex. | R¹ | B | m | p | A | Melting point(°C.) | MS(M⁺) | IR(cm⁻¹), NMR(ppm) |
|---|---|---|---|---|---|---|---|---|
| 23 | Cl | Ph | 2 | 1 | 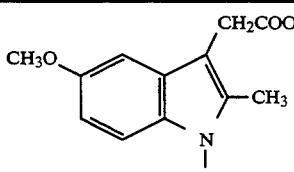 (5-CH₃O, 2-CH₃, 3-CH₂COOCH₃ indole) | — (amorphous) | 545 | IR(nujol): 1730 NMR(DMSO-d₆): 2.25(4H, brs), 2.31 (3H, s), 2.44(4H, brs), 2.50(2H, t), 3.54(3H, t), 3.73(3H, s), 4.12(2H, t), 4.27(1H, s), 6.66–7.44(12H, m) |
| 24 | Cl | Ph | 2 | 1 | 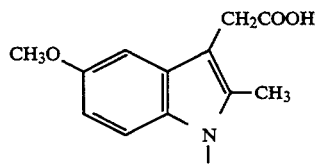 (5-CH₃O, 2-CH₃, 3-CH₂COOH indole) | Decomposition point 198 | 487 (Decarboxylated) | IR(nujol): 3350, 1700 NMR(DMSO-d₆): 2.36(3H, s), 2.50 (4H, brs), 2.80(2H, brs), 3.30 (4H, brs), 3.60(2H, s), 3.74(3H, s), 4.54(3H, brs), 6.72–7.45(12H, m), 11.36(1H, brs) |
| 25 | Cl | Ph | 2 | 1 | 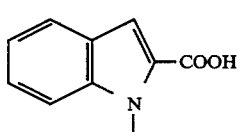 (indole-2-COOH) | Decomposition point 171–177 | 429 (Decarboxylated) | IR(nujol): 3400, 1590 NMR(DMSO-d₆): 2.28(4H, brs), 2.63(2H, t), 3.60(5H, brs), 4.27(1H, s), 4.68(2H, t), 7.09(1H, s), 7.00–7.62(13H, m) |
| 26 | Cl | Ph | 2 | 1 | 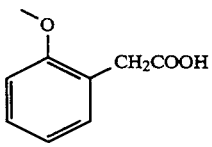 (2-methoxyphenyl-CH₂COOH) | Decomposition point 184 | 464 | IR(nujol): 3400, 1720, 1600 NMR(CDCl₃): 2.51(4H, brs), 2.76 (4H, brs), 2.92(2H, t), 3.56(2H, s), 4.11(2H, t), 4.22(1H, s), 5.45 (1H, brs), 6.77–7.36(13H, m) |
| 27 | Cl | Ph | 2 | 1 | 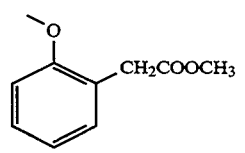 (2-methoxyphenyl-CH₂COOCH₃) | Decomposition point 168 | 478 | IR(nujol): 3400, 1720, 1590 NMR(DMSO-d₆): (2HCl)2.60(4H, brs), 2.98(4H, brs), 3.35(2H, t), 3.50 (3H, s), 3.66(2H, s), 4.38(2H, t), 4.82(1H, s), 6.94–7.53(13H, m) |

TABLE 6

| Ex. | R¹ | B | m | p | A | Melting point(°C.) | MS(M⁺) | IR(cm⁻¹), NMR(ppm) |
|---|---|---|---|---|---|---|---|---|
| 28 | Cl | Ph | 2 | 1 | 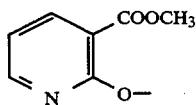 | 182–184 | 465 | IR(nujol): 3300, 1720, 1580 NMR(DMSO-d₆): (2HCl)2.87(4H, brs), 3.23(4H, brs), 3.57(2H, t), 3.77(3H, s), 4.67(1H, s), 4.73(2H, t), 7.16–8.41(12H, m) |

TABLE 6-continued

| Ex. | R¹ | B | m | p | A | Melting point(°C.) | MS(M⁺) | IR(cm⁻¹), NMR(ppm) |
|---|---|---|---|---|---|---|---|---|
| 29 | Cl | Ph | 2 | 1 | 2-O-linked pyridine-3-COOH | 173–174 | 451 | IR(nujol): 3150, 1700, 1580 NMR(DMSO-d₆): (2HCl)2.85 (4H, brs), 3.54(4H, brs), 3.66 (2H, t), 4.57(1H, s), 4.70(2H, t), 7.13–8.37(12H, m), 10.20(1H, brs) |
| 30 | Cl | Ph | 2 | 1 | 8-O-linked quinolin-2(1H)-one | Decomposition point 245–247 | 473 | IR(nujol): 3400, 1670, 1610 NMR(DMSO-d₆): (2HCl)3.22 (4H, brs), 3.76(8H, brs), 4.49(1H, s), 6.52–7.92 (14H, m), 11.12(1H, s) |
| 31 | Cl | Py | 2 | 1 | 2-methoxybenzoic acid | — (amorphous) | 451 | IR(nujol): 3350, 1690 NMR(DMSO-d₆): 2.35(4H, brs), 2.62(4H, brs), 2.75(2H, t), 4.23(2H, t), 4.45(1H, s), 6.97–7.78(11H, m), 8.44–8.46(1H, m) |
| 32 | Cl | Ph | 2 | 2 | methyl 2-methoxybenzoate | Decomposition point 157 (Dihydrochloride) | 478 | IR(nujol): 3400, 1720 NMR(DMSO-d₆): (2HCl)2.09(4H, m), 3.19(6H, m), 3.57(1H, s), 3.61(2H, t), 3.69(3H, s), 4.47(2H, t), 7.10–7.74(13H, m) |

TABLE 7

| Ex. | R¹ | B | m | p | A | Melting point(°C.) | MS(M⁺) | IR(cm⁻¹), NMR(ppm) |
|---|---|---|---|---|---|---|---|---|
| 33 | Cl | Ph | 2 | 2 | 2-methoxybenzoic acid | Decomposition point 164 (Dihydrochloride) | 464 | IR(nujol): 3350, 1700 NMR(DMSO-d₆): (2HCl)2.09 (4H, m), 3.29(6H, m), 3.57(1H, s), 3.60(2H, t), 4.47(2H, t), 7.05–7.73(14H, m) |
| 34 | H | Py | 2 | 1 | methyl 2-methoxybenzoate | — (oil) | 431 | IR(nujol): 1725 |
| 35 | H | Py | 2 | 1 | 2-methoxybenzoic acid | — (powder) | 417 | IR(nujol): 3350, 1708 NMR(DMSO-d₆): 2.36(4H, brs), 2.63(4H, brs), 2.76(2H, t), 4.23 (2H, t), 4.40(1H, s), 6.97–7.77 (12H, m), 8.30–8.44(1H, m) |
| 36 | Cl | Ph | 3 | 1 | —COOCH₂CH₃ | — (Oil) | 400 | IR(neat): 1730 NMR(DMSO-d₆): 1.16(3H, t), 1.61–1.69(2H, m), 2.08–2.50(10H, m), 3.31(2H, brs), 4.01(2H, q), 4.29(1H, s), 7.15–7.43(9H, m) |
| 37 | Cl | Ph | 3 | 1 | —COOH | Decomposition point 183–185 | 372 | IR(neat): 3400, 1710 NMR(DMSO-d₆): 1.57–1.68(2H, m), 2.21(2H, t), 2.30–2.43(8H, m), 2.40(2H, brs), 4.30(1H, s) 7.15–7.44(9H, m) |

TABLE 8

| Ex. | R¹ | B | m | p | A | Melting point(°C.) | MS(M+) | IR(cm⁻¹), NMR(ppm) |
|---|---|---|---|---|---|---|---|---|
| 38 | H | Ph | 2 | 2 | 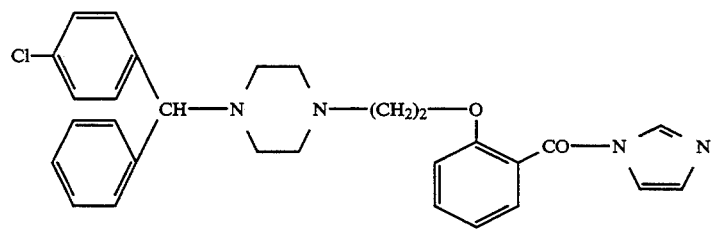 | 63–64 | 444 | IR(nujol): 3100, 1705, 1601<br>NMR(CDCl₃): 1.74–1.80(2H, m),<br>2.65(4H, dt), 2.82(2H, t),<br>2.92(2H, t), 3.30(2H, t),<br>3.82(3H, s), 4.14(2H, t)<br>4.59(1H, s), 6.94–7.79(14H, m) |
| 39 | H | Ph | 2 | 2 | 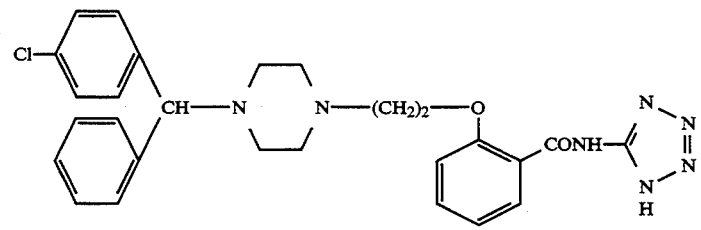 | — (foam)<br>(Dihydrochloride) | 429 | IR(neat): 3005, 1713, 1558<br>NMR(CDCl₃): 1.89–1.93(2H, m),<br>2.65(2H, t), 2.76(2H, t),<br>2.94(2H, t), 3.07(4H, dt),<br>4.37(2H, t), 4.57(1H, s),<br>5.33(1H, brs), 6.99–7.92(14H, m) |

EXAMPLE 40

2-[2-[4-[(4-Chlorophenyl)phenylmethyl]-1-piperazinyl]ethoxy]benzoylimidazole

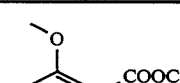

In dimethylformamide, 1.5 g (3.3 mmol) of 2-[2-[4-[(4-chlorophenyl)phenylmethyl]-1-piperazinyl]ethoxy]benzoic acid, which had been obtained in Example 4, were dissolved. Under ice cooling, 1.35 g (8.3 mmol) of carbodiimidazole were added to the resulting solution, followed by stirring at 80° C. for 20 minutes. After the reaction mixture was allowed to cool down, water was added and the resulting mixture was then extracted with ethyl ether. The ethyl ether layer was dried over anhydrous magnesium sulfate. The solvent was thereafter distilled off under reduced pressure. The residue so obtained was purified by chromatography on a column (chloroform), whereby the title compound was obtained. Melting point: powder (oxalate)

MS (m/z): 500(M+) IR (nujol) cm⁻¹: 1705 NMR (DMSO-d₆) δ: (oxalate) 2.38(2H,brs), 2.85(2H,brs), 3.12(2H,brs), 3.31(2H,brs), 3.40(2H,t), 4.34(2H,m), 4.48(1H,s), 6.95–7.68(13H,m), 7.97 (1H,s), 8.80(1H,s)

EXAMPLE 41

2- [2-[4-[(4-Chlorophenyl)phenylmethyl]-1-piperazinyl]ethoxy ]-N-1H-tetrazol-5-yl-benzamide

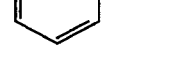

In dimethylformamide, 1.5 g (3.3 mmol) of the 2-[2-[4-[(4-chlorophenyl)phenylmethyl]-1-piperazinyl]-ethoxy]benzoic acid, which had been obtained in Example 4, were dissolved. Under ice cooling, 1.35 g (8.3 mmol) of carbodiimidazole were added to the resulting solution, followed by stirring at 80° C. for 20 minutes. The reaction mixture was allowed to cool down to room temperature. To the reaction mixture, 446 mg (4.3 mmol) of 5-amino-1H-tetrazole-H₂O were added, followed by stirring at 100° C. for one hour. The reaction mixture was poured into ice water to precipitate crystals. The crystals thus precipitated were collected by filtration and then purified by thin-layer chromatography, whereby 700 mg of the title compound were obtained. Yield: 39%

(Sodium salt)

Melting point (decomposition point): 178° C.

| Elemental analysis (1.2.H₂O) | | | |
|---|---|---|---|
| | C | H | N |
| Calculated: | 57.74 | 5.28 | 17.45 |
| Found: | 57.90 | 5.14 | 17.10 |

IR (nujol) cm⁻¹: 3300, 1660 NMR (DMSO-d6) δ: 2.06(4H,brs), 2.44(4H,brs), 2.74(2H,t), 4.05(1H,s), 4.29(2H,t), 7.05–7.93(14H,m)

(Hydrochloride)

Melting point (decomposition point): 197°–200° C.

MS (m/z): 517(M+) IR (nujol) cm⁻¹: 3400, 1680

EXAMPLE 42-59

In accordance with the procedures of Example 41, the compounds of Examples 42-59 shown in Tables 9-12 were obtained. The names of the compounds will be described below.

EXAMPLE 42
3-[2-[4-[(4-Chlorophenyl)phenylmethyl]-1-piperazinyl]ethoxy]-N-1H-tetrazol-5-yl-benzamide

EXAMPLE 43
[3-[4-(Diphenylmethyl)-1-piperazinyl]N-propionyl]-N-1H-tetrazol-5-yl-anthranilamide

EXAMPLE 44
2-[[2-[4-[(4-Chlorophenyl)phenylmethyl]-1-piperazinyl]ethyl]thio]-N-1H-tetrazol-5-yl-benzamide

EXAMPLE 45
2-[3-[4-[(4-Chlorophenyl)phenylmethyl]-1-piperazinyl]propoxy]-N-1H-tetrazol-5-yl-benzamide

EXAMPLE 46
2-[3-[4-(Diphenylmethyl)-1-piperazinyl]propoxy]-N-1H-tetrazol-5-yl-benzamide

EXAMPLE 47
1-[2-[4-[(4-Chlorophenyl)phenylmethyl]-1-piperazinyl]ethoxy]-N-1H-tetrazol-5-yl-naphthoamide

EXAMPLE 48
2-[2-[4-[(4-Chlorophenyl)phenylmethyl]-1-piperazinyl]ethoxy]-N-1H-tetrazol-5-yl-naphthoamide

EXAMPLE 49
2-[4-[(4-Chlorophenyl)phenylmethyl]-1-piperazinyl]ethyl]-N-1H-tetrazol-5-yl-anthranilamide

EXAMPLE 50
2-[2-[4-[(4-Chlorophenyl)phenylmethyl]-1-piperazinyl]ethoxy]-N-1H-tetrazol-5-yl-acetamide

EXAMPLE 51
1-[2-[4-[(4-Chlorophenyl)phenylmethyl]-1-piperazinyl]ethyl]-N-1H-tetrazol-5-yl-3-indoleamide

EXAMPLE 52
1-[2-[4-[(4-Chlorophenyl)phenylmethyl]-1-piperazinyl]ethyl]-N-1H-tetrazol-5-yl-2-indoleamide

EXAMPLE 53
2-[2-[4-[(4-Chlorophenyl)phenylmethyl]-1-piperazinyl]ethoxy]-N-1H-tetrazol-5-yl-phenylacetamide

EXAMPLE 54
2-[2-[4-[(4-Chlorophenyl)phenylmethyl]-1-piperazinyl]ethoxy]-N-1H-tetrazol-5-yl-nicotinamide

EXAMPLE 55
2-[2-[4-[(2-Phenyl-pyridylmethyl]-1-piperazinyl]ethoxy]-N-1H-tetrazol-5-yl-benzoic acid amide

EXAMPLE 56
2-[2-[4-(Diphenylmethyl)-1-piperazinyl]ethoxy]-N-1H-tetrazol-5-yl-benzamide

EXAMPLE 57
2-[2-[4-[2-(4-Chlorophenyl)pyridylmethyl]-1-piperazinyl]ethoxy]-N-1H-tetrazol-5-yl-benzoic acid amide

EXAMPLE 58
2-[4-[(4-Chlorophenyl)phenylmethyl]-1-homopiperazinyl]ethoxy]-N-1H-tetrazol-5-yl-benzamide

EXAMPLE 59
2-[2-[4-(Diphenylmethyl)-1-homopiperazinyl]-ethoxy]-N-1H-tetrazol-5-yl-benzamide

TABLE 9

| EX. | R¹ | B | m | p | A | Melting point(°C.) | MS(M⁺) | IR(cm⁻¹), NMR(ppm) |
|---|---|---|---|---|---|---|---|---|
| 42 | Cl | Ph | 2 | 1 | (3-O-phenyl-CONH-tetrazole) | Decomposition point 178 | 518 | IR(nujol):3175, 1640 NMR(DMSO-d₆):2.32(4H, brs), 2.56 (2H, brs), 2.75(2H, t), 3.45(2H, brs), 4.14(2H, t), 4.31(1H, s), 7.16–7.46(12H, m), 7.63(2H, brs) |
| 43 | H | Ph | 2 | 1 | (2-CONH-phenyl-CONH-tetrazole) | — (powder) | | NMR(DMSO-d₆):2.22(2H, brs), 2.35 (2H, brs), 2.76(2H, t), 3.18(2H, brs), 4.23(2H, t), 4.33(1H, t), 6.88(1H, s), 7.16–7.44(14H, m), 7.61(1H, s), 9.65(1H, s) |
| 44 | Cl | Ph | 2 | 1 | (2-S-phenyl-CONH-tetrazole) | 190–193 (Dihydrochloride) | 533 | IR(nujol):3200, 1690 NMR(DMSO-d₆):(2HCl)2.89(4H, brs), 3.17(1H, s), 3.26(2H, t), 3.38(2H, t), 3.90(4H, brs), 4.84(1H, s), 7.27–7.76(13H, m), 11.89(1H, s) |

TABLE 9-continued

| EX. | R¹ | B | m | p | A | Melting point(°C.) | MS(M⁺) | IR(cm⁻¹), NMR(ppm) |
|---|---|---|---|---|---|---|---|---|
| 45 | Cl | Ph | 3 | 1 | 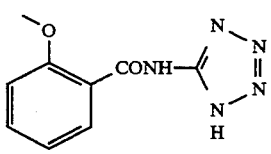 | — (Powder) | | IR(nujol):3350, 1650<br>NMR(DMSO-d₆):1.96(2H, brs), 2.29 (2H, brs), 2.40–2.60(4H, m), 3.48 (6H, brs), 4.19(2H, t), 4.29(1H, s), 7.07–7.52(12H, m), 7.80(1H, brs) |
| 46 | H | Ph | 3 | 1 | 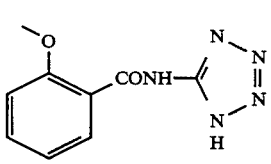 | 194–199 (Dihydrochloride) | 497 | IR(nujol):2450, 1680<br>NMR(DMSO-d₆);(2HCl)2.20(2H, t), 3.32(3H, brs), 3.63(8H, brd), 4.21(2H, t), 7.08–7.75(15H, m), 11.88(1H, s) |

TABLE 10

| Ex. | R¹ | B | m | p | A | Melting point(°C.) | MS(M⁺) | IR(cm⁻¹), NMR(ppm) |
|---|---|---|---|---|---|---|---|---|
| 47 | Cl | Ph | 2 | 1 | 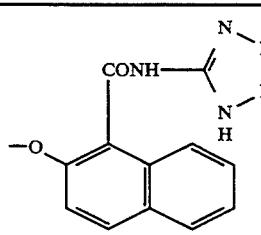 | | 567 | IR(nujol): 3400, 1670, 1600<br>NMR(DMSO-d₆): 2.25(4H, brs), 2.64(4H, brs), 2.86(2H, t), 4.26(1H, s), 4.36(12H, t), 7.18–8.09(17H, m) |
| 48 | Cl | Ph | 2 | 1 | 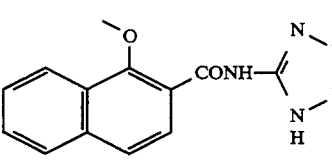 | Decomposition point 196–197 (Dihydrochloride) | 567 | IR(nujol): 2400, 1680, 1580<br>NMR(DMSO-d₆): (2HCl)2.83(4H, brs), 3.61(2H, t), 3.80(4H, brs), 4.43(2H, t), 4.65(1H, s), 7.35–8.19(16H, m), 12.51(1H, brs) |
| 49 | Cl | Ph | 2 | 1 | 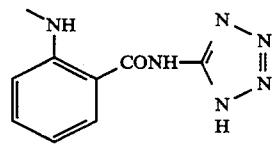 | Decomposition point 171 | 516 | NMR(DMSO-d₆): 2.33(4H, brs), 2.89(4H, brs), 3.27(2H, t), 3.88 (2H, t), 4.27(1H, s), 6.59–6.78(2H, m), 6.96(1H, s), 7.18–7.50(10H, m), 7.83–7.86(1H, m), 10.79(1H, s) |
| 50 | Cl | Ph | 2 | 1 | 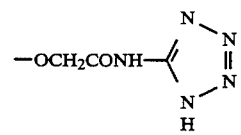 | Decomposition point 168 (Dihydrochloride) | 455 | IR(nujol): 3400, 3170, 1700<br>NMR(DMSO-d₆): (2HCl)2.09(2Hs), 3.10(4H, brs), 3.46(2H, t), 3.65 (4H, brs), 3.94(2H, brs), 4.30(2H, s), 7.34–7, 48(5H, m), 7.76(7H, brs) |
| 51 | Cl | Ph | 2 | 1 | 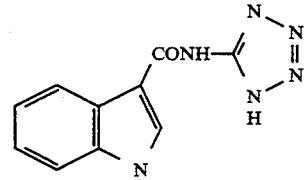 | Decomposition point 162 | 540 | IR(nujol): 3200, 1670<br>NMR(DMSO-d₆): 2.27(4H, brs), 2.73(2H, t), 3.50(4H, brs), 4.28 (1H, s), 4.35–4.47(2H, m), 7.15–8.56(15H, m), 11.88(1H, s) |

TABLE 11

| Ex. | R¹ | B | m | p | A | Melting point (°C.) | MS(M⁺) | IR(cm⁻¹), NMR(ppm) |
|---|---|---|---|---|---|---|---|---|
| 52 | Cl | Ph | 2 | 1 | 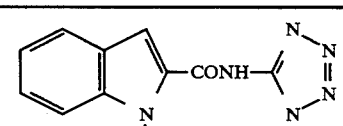 | Decomposition point 163 | 540 | IR(nujol):3400, 3200, 1650<br>NMR(DMSO-d₆):2.16(4H, brs),<br>NMR(DMSO-d₆):2.16(4H, brs), 2.41 (4H, brs), 2.56(2H, t), 4.07(1H, s), 4.67(2H, t), 6.97–7.68(16H, m) |

TABLE 11-continued

| Ex. | R¹ | B | m | p | A | Melting point (°C.) | MS(M+) | IR(cm⁻¹), NMR(ppm) |
|---|---|---|---|---|---|---|---|---|
| 53 | Cl | Ph | 2 | 1 | 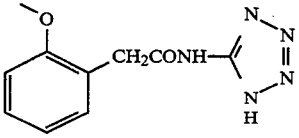 | 161 | 531 | IR(nujol):3200, 1670, 1580 NMR(DMSO-d₆):2.24(4H, brs), 2.67 (4H, brs), 3.55(2H, t), 3.70 (2H, s), 4.03(2H, t), 4.22(1H, s) 6.89–7.80(14H, m), 11.88(1H, brs) |
| 54 | Cl | Ph | 2 | 1 | 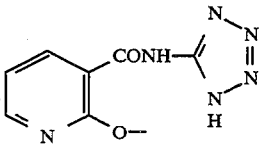 | 140–141 | 518 | IR(nujol:3350, 1670, 1570 NMR(DMSO-d₆):2.25(4H, brs), 2.58(4H, brs), 2.84(2H, t), 4.21(1H, s), 4.56(2H, t) 7.17–8.40(14H, m) |
| 55 | H | Py | 2 | 1 | 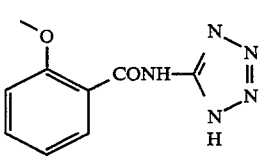 | — (powder) | 484 | IR(nujol):3250, 3150 NMR(DMSO-d₆):2.16(4H, brs), 2.78 (2H, t), 3.51(4H, brs), 4.22(1H, s) 4.31(2H, t), 6.56(1H, s), 7.07–7.92 (12H, m), 8.39(1H, m), 10.70(1H, brs) |
| 56 | H | Ph | 2 | 1 | 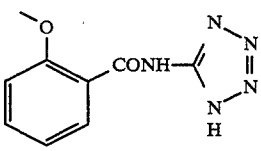 | Decomposition point 176 | 483 | IR(nujol):3190, 1660, 1550 NMR(DMSO-d₆):2.24(4H, brs), 2.58(4H, brs), 2.83(2H, t) 4.13(1H, s), 4.33(2H, t), 7.12–8.25(16H, m) |

TABLE 12

| Ex. | R¹ | B | m | p | A | Melting point (°C.) | MS(M+) | IR(C⁻¹), NMR(ppm) |
|---|---|---|---|---|---|---|---|---|
| 57 | Cl | Py | 2 | 1 | 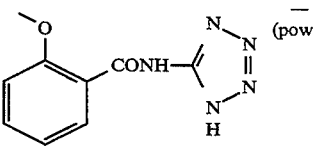 | — (powder) | 518 | IR(nujol):3250, 1640 NMR(DMSO-d₆):2.12(4H, brs), 2.76(2H, t), 3.42(4H, brs), 4.23(1H, s), 4.30 (2H, t), 6.55(1H, s), 7.09–7.88(9H, m), 8.40–8.42(1H, m), 10.70(1H, brs) |
| 58 | Cl | Ph | 2 | 2 | 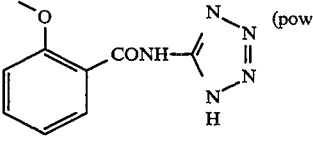 | — (powder) | 531 | IR(nujol):3350, 1670 NMR(DMSO-d₆):1.66(2H, brs), 2.56(2H, t), 3.00(4H, brs), 3.10(4H, brs), 4.35(2H, t), 4.62(1H, s), 6.97–7.72(15H, m) |
| 59 | H | Ph | 2 | 2 | 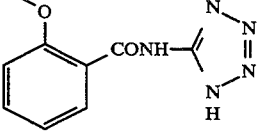 | 99–100 | 497 | NMR(CDCl₃):1.78–1.93(2H, m), 2.58 (2H, t), 2.64(2H, t), 2.97(2H, t), 3.02(2H, t), 3.11(2H, t), 4.35 (2H, t), 4.58(1H, s), 5.96(1H, brs), 6.67–8.08(14H, m), 10.78(1H, brs) |

EXAMPLE 60

2-[2-[4-[(4-Chlorophenyl)phenylmethyl]-1-piperazinyl-]ethoxy]-N-3,4,5-trimethoxyphenyl-benzamide

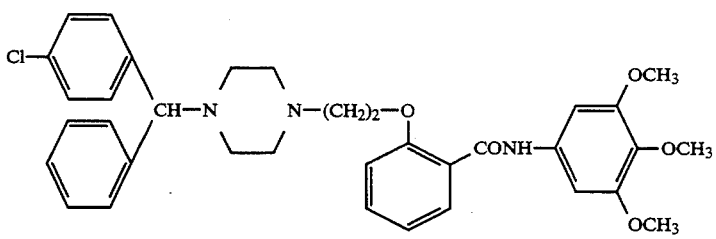

In 30 ml of ethyl acetate, 676 mg (3.67 mmol) of 3,4,5-trimethoxyaniline were dissolved. An aqueous solution (20 ml), in which were dissolved 2.0 g (3.69 mmol) of 2-[2-[4-[(4-chlorophenyl)phenylmethyl]-1-piperazinyl]ethoxy]benzoic acid chloride.dihydrochloride and 1.24 g of sodium hydrogencarbonate, was added to the resulting solution under ice cooling, followed by stirring for 30 minutes under ice cooling. The ethyl acetate layer was collected, washed successively with 10% sodium hydroxide and water and then, dried over anhydrous magnesium sulfate. The solvent was distilled off under reduced pressure. Crude crystals so obtained were recrystallized from a mixed solvent of chloroform and isopropyl ether, whereby 1.75 g of the title compound were obtained. Yield: 77%.

Melting point (decomposition point): 157°–158° C. MS (m/z): 615(M+) IR (nujol) cm$^{-1}$: 3320, 1655 NMR (DMSO-d6) δ:

2.16(4H,brs), 2.50(4H,brs), 2.78(2H,t),
3.66(3H,s), 3.73(6H,s), 4.09(1H,s), 4.25(2H,t),
7.03 (2H, s), 7.07–7.78(13H,m), 10.08(1H,s)

EXAMPLES 61–65

Following the procedures of Example 60, the compounds of Examples 61–65 shown in Table 13 were obtained. The followings are the names of the compounds:

EXAMPLE 61

2-[2-[4-[(4-Chlorophenyl)phenylmethyl]-1-piperazinyl]ethoxy]-N-(3,5-dimethyl-4-hydroxyphenyl)-benzamide

EXAMPLE 62

2-[2-[4-[(4-Chlorophenyl)phenylmethyl]-1-piperazinyl]ethoxy]-thiazolidyl-2-yl-benzamide

EXAMPLE 63

2-[2-[4-[(4-Chlorophenyl)phenylmethyl]-1-piperazinyl]ethoxy]-thiazol-2-yl-benzamide

EXAMPLE 64

2-[2-[4-[(4-Chlorophenyl)phenylmethyl]-1-piperazinyl]ethoxy]-N-1H-triazol-5-yl-benzamide

EXAMPLE 65

2-[2-[4-(4-Chlorophenyl)phenylmethyl]-1-piperazinyl]ethoxy]benzamide

TABLE 13

| Ex. | R$^1$ | B | m | p | A | Melting point (°C.) | MS(M+) | IR(cm$^{-1}$), NMR(ppm) |
|---|---|---|---|---|---|---|---|---|
| 61 | Cl | Ph | 2 | 1 | (2-methoxyphenyl-CONH-3,5-dimethyl-4-hydroxyphenyl) | Decomposition point 198–200 | 569 | NMR(DMSO-d$_6$):2.15(10H, brs), 2.50(4H, brs), 2.77(2H, t), 4.03(1H, s), 4.26(2H, t), 7.05–7.51(14H, m), 7.86–7.90(1H, m), 8.13(1H, brs), 9.95(1H, s) |
| 62 | Cl | Ph | 2 | 1 | (2-methoxyphenyl-CONH-thiazolidinyl) | — (foam) | 535 | IR(nujol):3300, 1670 |
| 63 | Cl | Ph | 2 | 1 | (2-methoxyphenyl-CONH-thiazolyl) | 136–138 | 533 | IR(nujol):3250, 1645 NMR(DMSO-d$_6$):2.24(4H, brs), 2.51(4H, brs), 2.77(2H, t), 4.18 (1H, s), 4.33(2H, t), 7.07–7.59 (14H, m), 7.85–7.88(1H, m) |
| 64 | Cl | Ph | 2 | 1 | (2-methoxyphenyl-CONH-triazolyl) | — (powder) | 517 | IR(nujol):3300, 1660 NMR(DMSO-d$_6$):2.17(4H, m), 2.50 (4H, m), 2.75(2H, t), 4.12(1H, s), 4.31(2H, t), 7.08–7.40(13H, m), 7.52–7.59(1H, m), 7.85–7.89(1H, m) |

TABLE 13-continued

| Ex. | R¹ | B | m | p | A | Melting point (°C.) | MS(M+) | IR(cm⁻¹), NMR(ppm) |
|---|---|---|---|---|---|---|---|---|
| 65 | Cl | Ph | 2 | 1 | (2-methoxy-benzamide structure) | 160–161 | 449 | IR(nujol):3400, 1660 NMR(DMSO-d$_6$):2.31(4H, brs), 2.49(4H, brs), 2.71(2H, t), 4.20(2H, t), 4.29(1H, s), 6.99–7.88(13H, m), 8.20(2H, brs) |

EXAMPLE 66

2-[[2-[4-[(4-Chlorophenyl)phenylmethyl]-1-piperazinyl]ethyl]amino]benzoic acid

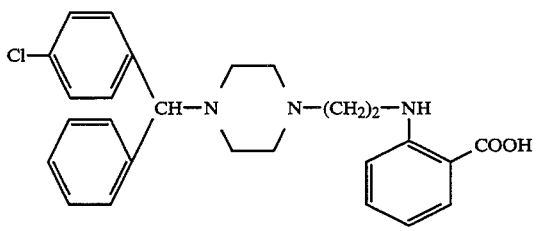

In 1N sodium hydroxide, 800 mg (1.74 mmol) of the 1-[2-[4-[(4-chlorophenyl)phenylmethyl]-1-piperazyl]ethoxy]isatin, which had been obtained according to the procedures of Example 1, and 3 ml of tetrahydrofuran were dissolved, followed by the dropwise addition of 1 ml of a 30% aqueous hydrogen peroxide solution. After having been stirred at 70° C. for one hour, the reaction mixture was allowed to cool down and an aqueous solution of sodium sulfite was added. Further, acetic acid was added to the resulting mixture to adjust its pH to 3. Crystals so precipitated were purified by chromatography on a silica gel column (ethyl acetate), whereby 405 mg of the title compound were obtained. Yield: 52%.

Melting point: 205°–206° C.
MS (m/z): 449(M+)
IR (nujol) cm⁻¹: 3320, 1655 NMR ( DMSO-d$_6$ ) δ: 2.32(4H,brs), 2.50(4H,brs), 2.58(2H,t), 3.21(2H,t), 4.27(1H,s), 6.52(1H,t), 6.79(1H,d), 7.18(1H,d), 7.26–7.46(11H,m), 7.76(1H,dd)

EXAMPLE 67

Sodium 2-[[2-[4-[(4-chlorophenyl)phenylmethyl ]-1-piperazinyl]ethyl]amino]-α-oxo-phenylacetate

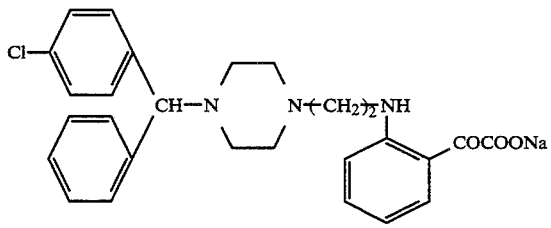

In 5 ml of tetrahydrofuran, 300 mg of 1-[2-[4-[(4-chlorophenyl)phenylmethyl]-1-piperazyl]ethoxy]-isatin, which had been obtained in accordance with the procedures of Example 1, and 0.5 ml of a 1N aqueous sodium hydroxide solution were dissolved, followed by stirring at room temperature for 2 hours. The solvent was distilled off under reduced pressure. The residue was thereafter dissolved in water and purifed on poly- styrene gel (HP-20), whereby the title compound was obtained.

Melting point (decomposition point): 130°–133° C. (sodium salt)

| | Elemental analysis: | | |
|---|---|---|---|
| | C | H | N |
| Calculated: | 64.86 | 5.44 | 8.40 |
| Found: | 64.83 | 5.70 | 8.17 |

EXAMPLE 68

2-[2-[4-[(4-Chlorophenyl)phenylmethyl]-1-piperazinyl]ethoxy]-(N-1H-tetrazol-5-yl)-benzene In 50 ml of toluene, 4.7 g (10.9 mmol) of the 2-[2-[4-[(4-chlorophenyl)phenylmethyl]-1-piperazinyl]-ethoxy]benzonitrile, which had been obtained in Example 13, and 10.9 g (32.7 mmol) of tri-n-butyltin azide were dissolved, followed by refluxing for two days. To the reaction mixture, 5.6 g of benzonitrile were added, followed by further refluxing until the excess tri-n-butyltin azide was eliminated. After the reaction mixture was allowed to cool down, the solvent was distilled off under reduced pressure. The residue so obtained was dissolved in a mixed solution of hydrochloric acid, dioxane and ethanol, followed by stirring for one hour. After the solvent was distilled off, a mixed solution of toluene and ethyl ether was added, whereby 4.34 g of the title compound were obtained as a precipitate. Yield: 72%.

Melting point: powder (dihydrochloride) MS (m/z): 474(M+) IR (nujol) cm⁻¹: 3400 NMR (DMSO-d6) δ: 2.41(2H,m), 2.65(7H,m), 2.86–2.92(2H,m), 4.19(2H,t), 4.32(2H,t), 6.92–7.54(14H,m), 8.31–8.34 (1H,m)

EXAMPLES 69 & 70

Following the procedures of Example 68, the compounds of Examples 68 and 69 shown in Table 14 were obtained. The followings are the names of the compounds:

EXAMPLE 69

2-[2-[4-[(4-Chlorophenyl)phenylmethyl]-1-piperazinyl]ethoxy]-1-tetrazol-5-ylmethyl

EXAMPLE 70

3-[2-[4-[(4-Chlorophenyl)phenylmethyl]-1-piperazinyl]ethoxy]-[N-1H-tetrazol-5-yl]-benzene nesium sulfate and the solvent was distilled off. The residue so obtained was purified by chromatography on a silica gel column (chloroform: methanol =10:1), whereby 2.8 g of the title compound were obtained in an oily form. Yield: 51%.

Melting point: 181–184° C. (hydrochloride) MS (m/z): 466(M+) IR (nujol) cm$^{-1}$: 2280, 1700, 1590 NMR (DMSO-d6) δ: (dihydrochloride) 3.09(4H,brs),

TABLE 14

| Ex. | R$^1$ | B | m | p | A | Melting point (°C.) | MS(M+) | IR(cm$^{-1}$), NMR(ppm) |
|---|---|---|---|---|---|---|---|---|
| 69 | Cl | Ph | 2 | 1 | 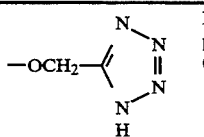 | Decomposition point 225 (Dihydrochloride) | 412 | IR(nujol):3450 NMR(DMSO-d$_6$):(2HCl)2.60–3.80(11H, m), 3.95(2H, t), 4.91(2H, s), 7.38–7.48 (5H, m), 7.77(4H, brs) |
| 70 | Cl | Ph | 2 | 1 | 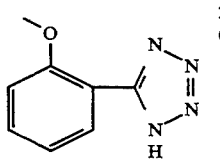 | 220–222 (Dihydrochloride) | 474 | IR(nujol):3400 NMR(DMSO-d$_6$):(2HCl)3.14(4H, brs), 3.20–4.50(9H, m), 4.54(2H, brs), 5.33(1H, brs), 7.20–7.75(13H, m) |

EXAMPLE 71

2-[[2-[4-[(4-Chlorophenyl)phenylmethyl]-1-piperazinyl]ethyl]thio]benzoic acid

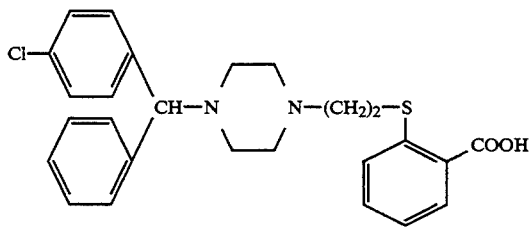

In a 15:85 mixed solution of water and tetrahydrofuran, 5.0 g (12 mmol) of 2-[4-[(4-chlorophenyl)phenylmethyl]-1-piperazinyl]-ethylchloride.dihydrochloride were dissolved, followed by the dropwise addition of 4.0 g (39 mmol) of triethylamine under an argon stream.

3.35(4H,brs), 3.41(2H,t), 3.60(3H,t), 3.64(1H,s), 7.24–7.93(14H,m)

EXAMPLES 72–74

In accordance with the procedures of Example 71, the compounds of Examples 72–74 shown in Table 15 were obtained. The followings are the names of the compounds.

EXAMPLE 72

Ethyl 2-[[2-[4-[(4-Chlorophenyl)phenylmethyl]-1-piperazinyl]ethyl]thio]acetate

EXAMPLE 73

2-[[2-[4-[(4-Chlorophenyl)phenylmethyl]-1-piperazinyl]ethyl]thio]acetic acid

EXAMPLE 74

2-[[2-[4-[(4-Chlorophenyl)phenylmethyl]-1-piperazinyl]ethyl]thio]nicotinic acid

TABLE 15

| Ex. | R$^1$ | B | m | p | A | Melting point (°C.) | MS(M+) | IR(cm$^{-1}$), NMR(ppm) |
|---|---|---|---|---|---|---|---|---|
| 72 | Cl | Ph | 2 | 1 | —S—CH$_2$COOCH$_2$CH$_3$ | — (powder) (Oxalate) | 432 | NMR(DMSO-d$_6$):(oxalate)1.21(3H, t), 2.98–3.04(2H, m), 3.26(4H, brs), 3.37–3.42(2H, m), 3.50 (2H, s), 3.65(5H, brs), 4.12(2H, q), 7.35–7.51(4H, m), 7.87(5H, t) |
| 73 | Cl | Ph | 2 | 1 | —S—CH$_2$COOH | Decomposition point 170–172 (Oxalate) | 404 | IR(nujol):3450, 1720 NMR(DMSO-d$_6$):(oxalate)2.50 (4H, m), 2.86–2.91(2H, m), 3.20–3.26(6H, m), 3.36(2H, s), 4.50 (1H, s), 7.23–7.48(9H, m) |
| 74 | Cl | Ph | 2 | 1 | 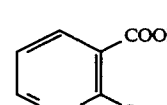 | 185 (Dihydrochloride) | 467 | IR(nujol):3400, 1720, 1560 NMR(DMSO-d$_6$):(2HCl)2.93 (4H, brs), 3.39(4H, brs), 3.60 (2H, t), 4.62(3H, brs), 7.25–8.70(13H, m) |

To the resulting solution, 2.2 g (14 mmol) of thiosalicylic acid were added and they were stirred at 50° C. for 8 hours. After the reaction mixture was allowed to cool down, the solvent was distilled off under reduced pressure. Water (200 ml) was added to the residue, followed by extraction with 200 ml of ethyl acetate. The ethyl acetate layer was dried over anhydrous mag-

EXAMPLE 75

Methyl 2-[2-[4-[(4-chlorophenyl)phenylmethyl]-1-piperazinyl]ethyl]thio]benzoate

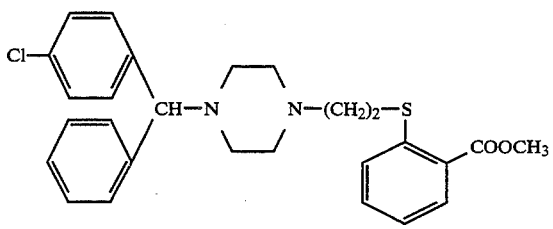

In 20 ml of anhydrous dichloromethane, 1.1 g (2.36 mmol) of the 2-[[2-[4-[(4-chlorophenyl)phenylmethyl]-1-piperazinyl]ethyl]thio]benzoic acid, which had been obtained in Example 71, were suspended, followed by the dropwise addition of 0.4 g (3.53 mmol) of thionyl chloride and stirring for 30 minutes, both under ice cooling. After the solvent was distilled off under reduced pressure, 20 ml of anhydrous methanol were added to the residue and the resulting mixture was stirred at room temperature for 30 minutes. The solvent was distilled off under reduced pressure. Water (50 ml) was added to the residue, followed by extraction with 50 ml of ethyl acetate. The ethyl acetate layer was washed with a saturated aqueous solution of sodium hydrogencarbonate and then dried over anhydrous magnesium sulfate. The solvent was distilled off under reduced pressure. The residue so obtained was purified by chromatography on a silica gel column (ethyl acetate:n-hexane =2:1), whereby 0.94 g of the title compound was obtained in an oily form. Yield: 85%.

Melting point: 170°–171° C. (hydrochloride) MS (m/z): 480(M+) IR (nujol) cm$^{-1}$: 2300, 1710, 1590 NMR (DMSO-d$_6$) δ: (dihydrochloride) 2.38(4H,brs), 2.80(4H,brs), 3.17 (2H,t), 3.45(2H,t), 3.83(3H,s), 4.53(1H,s), 7.20–7.92(13H,m)

EXAMPLE 76

Methyl [3-[4-(diphenylmethyl)-1-piperazinyl]N-propionyl]anthranilate

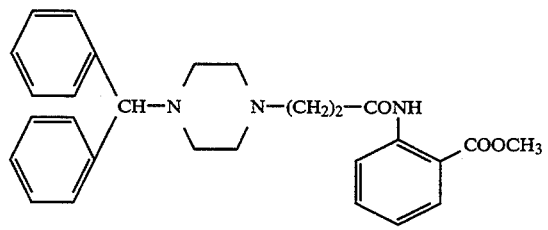

In 100 ml of toluene, 5.92 g (23.5 mmol) of diphenylmethylpiperazine, 5.67 g (23.5 mmol) of methyl N-3-chloropropionylanthranilate and 6.23 g (43.9 mmol) of sodium carbonate were suspended, followed by refluxing for 12 hours. The reaction mixture was allowed to cool down and water was added to it, followed by extraction with ethyl acetate. The ethyl acetate layer was washed with water and then dried over anhydrous magnesium sulfate. The solvent was distilled off under reduced pressure. The residue so obtained was purified by chromatography on a silica gel column (n-hexane: ethyl acetate =1:2), whereby 9.2 g of the title compound were obtained. Yield: 86%.

Melting point: 120°–122° C. MS (m/z): 457(M+) IR (nujol) cm$^{-1}$: 3280, 1710, 1690 NMR (DMSO-d6) δ: 2.31(4H,brs), 2.48(4H,brs), 2.50(2H,t), 3.80(3H,s), 4.24(1H,s), 7.13–8.27(14H,m)

| Preparation Example 1 | |
|---|---|
| Compound of Example 41 | 50 g |
| Lactose | 315 g |
| Corn starch | 125 g |
| Crystalline cellulose | 25 g |

The above ingredients were mixed uniformly, followed by the addition of 200 ml of a 7.5% aqueous solution of hydroxypropylcellulose. The resultant mixture was granulated through a screen of 0.5 mm in diameter by an extrusion granulator. Immediately after that, the resultant granules were rounded by a Marumerizer and then dried, whereby granules were obtained.

The dried granules so obtained were coated with 1.9 kg of a film coating solution of the below-described composition by using a fluidized-bed granulator, whereby enteric coated granules were obtained.

| Composition of the coating solution: | |
|---|---|
| Hydroxypropylmethylcellulose phthalate | 5.0 wt. % |
| Stearic acid | 0.25 wt. % |
| Methylene chloride | 50.0 wt. % |
| Ethanol | 44.75 wt. % |
| Preparation Example 2 | |
| Compound of Example 45 | 20 g |
| Lactose | 100 g |
| Corn starch | 36 g |
| Crystalline cellulose | 30 g |
| Carboxymethylcelullose calcium | 10 g |
| Magnesium stearate | 4 g |

The above ingredients were mixed uniformly and then, pressed into 200-mg tablets by a punch of 7.5 mm in diameter on a single punch tableting machine.

A coating solution of the below composition was sprayed to the tablets to apply 10 mg of a coating per tablet, whereby enteric film-coated tablets were obtained.

| Composition of the coating solution: | |
|---|---|
| Hydroxypropylmethylcellulose phthalate | 8.0 wt. % |
| Glycerin fatty acid ester | 0.4 wt. % |
| Methylene chloride | 50.0 wt. % |
| White beeswax | 0.1 wt. % |
| Isopropanol | 41.5 wt. % |
| Preparation Example 3 | |
| Compound of Example 46 | 100 mg |
| Sodium acetate | 2 mg |
| Acetic acid | q.s. |
| (for adjustment of pH to 5.8) | |
| Distilled water for injection | q.s. |
| Total | 10 ml/vial |

An injection was obtained according to the above formulation in a manner known per se in the art.

| Preparation Example 4 | |
|---|---|
| Compound of Example 69 | 0.1 wt. % |
| Ethanol | 20.0 wt. % |
| Liquefied gas ("Propellant 114") | 49.2 wt. % |
| Liquefied gas ("Propellant 12") | 30.7 wt. % |

An aerosol was prepared according to the above formulation in a manner known per se in the art.

Tests

Test 1 Antihistamic effects

From a Hartley male guinea pig (300–600 g in weight), the ileum was isolated. The ileum was attached to a holder under a vesting tension of 0.5 g in a Magnus bath (30° C., under aeration) filled with 10 ml of the Tyrode solution. As a contraction reaction of the isolated ileum caused by histamine ($3 \times 10^{-7}$ mole), an isometrical change in muscular tension was measured. The ileum was treated with the test compound for 3 minutes before the addition of histamine to study its effects and then its antihistamic action (50% inhibition concentration: $IC_{50}$ value) was determined.

As a result, each compound showed an $IC_{50}$ value of from 0.14 to 1.59 μM. Incidentally, the $IC_{50}$ value of Cetirizine (the compound disclosed in Japanese Patent Laid-Open No. 149282/1982) was determined as a control. Its IC value was 2.40 μM.

Test 2 Antiallergic effects

The back of a male SD rat (150–250 g in weight) was shaved in advance. Physiological saline and 0.1 ml of anti DNP-AS (Dinitrophenyl conjugated Ascaris) IgE serum which had been diluted to a suitable concentration with physiological saline were intradermally injected there. Fourty-eight hours after sensitization, the animals were challenged with 1 ml of 0.5% Evans blue physiological saline containing 2.5 mg/ml of DNP-BSA (dinitrophenyl conjugated bovine serum albumin) via the tail vein. Thirty minutes later, they were sacrificed under exsanguination and the dorsal skin was removed and the exuded dye was measured according to the method proposed by Harada et al. [Allergy, 15, 1–7(1966)]. The leaked color amount caused by the passive cutaneous anaphylaxis (PCA) was determined by subtracting the leaked color amount of the site to which physiological saline was administered from that of the PCA site. Each test compound was suspended in 5% gum arabic or 0.5% methylcellulose and the-resulting suspension was orally administered at the rate of 10 mg/4 ml/kg one hour before the administration of antigen. The efficacy of the test compound was evaluated by an ihibition rate (antiallergic effects) of the leaked color amount. The results are shown in Table 16.

TABLE 16

| Test compound | Antiallergic effects (%) |
| --- | --- |
| Compound of Example 5 (½ fumarate) | 86.4 |
| Compound of Example 9 | 61.9 |
| Compound of Example 41 (Sodium salt) | 52.3 |
| Compound of Example 44 | 54.7 |
| Compound of Example 45 | 72.4 |
| Compound of Example 46 | 59.8 |
| Compound of Example 50 | 60.4 |
| Compound of Example 69 | 81.0 |

Test 3 Toxicity Test

Ten 4–5 week old ICR mice (Charles River Co., Ltd.) were employed in groups, each consisting of 10 mice. The compounds of the Examples were separately suspended in 5% gum arabic. The suspension were each orally administered at a dose of 1000 mg/kg and the mice were observed for 7 days. As a result, no case of death caused by the toxicity of any of the invention compounds was observed.

Industrial Applicability

The compounds according to the present invention have strong antihistamic and antiallergic effects and have a high degree of safety so that they are useful as therapeutic agents for various allergic diseases, for example, as anti-inflammatory agents, therapeutics for nephritis, hepatitis or pancreatitis, preventives and/or therapeutics for respiratory diseases, and anti-asthmatic drugs.

What is claimed is:

1. A compound of formula (1):

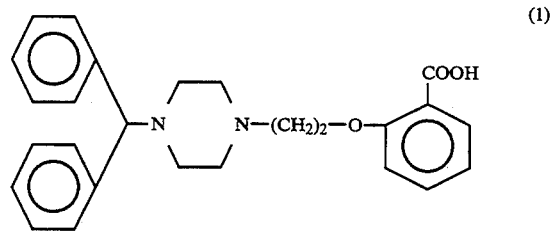

or a pharmaceutically acceptable salt thereof.

2. A pharmaceutical composition comprising an effective amount of a compound of formula (1) as claimed in claim 1 or a pharmaceutically acceptable salt thereof and a pharmaceutically acceptable auxiliary agent.

3. A method for treatment of allergic diseases, which method comprises administering an effective amount of a compound of formula (1):

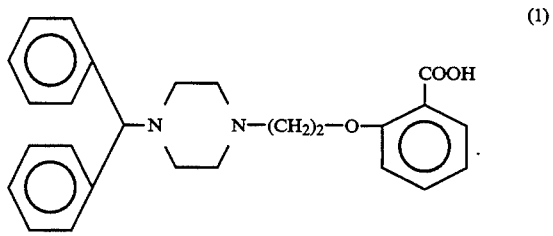

or a pharmaceutically acceptable salt thereof to a patient suffering from allergic disease.

4. A method as claimed in claim 3 wherein said allergic disease is bronchial asthma.

* * * * *